(12) United States Patent
Traneus

(10) Patent No.: US 11,344,746 B2
(45) Date of Patent: May 31, 2022

(54) SYSTEM AND METHOD FOR ION BASED RADIOTHERAPY TREATMENT PLANNING

(71) Applicant: RaySearch Laboratories AB, Stockholm (SE)

(72) Inventor: Erik Traneus, Uppsala (SE)

(73) Assignee: RAYSEARCH LABORATORIES AB, Stockholm (SE)

( * ) Notice: Subject to any disclaimer, the term of this patent is extended or adjusted under 35 U.S.C. 154(b) by 270 days.

(21) Appl. No.: 16/608,504

(22) PCT Filed: May 3, 2017

(86) PCT No.: PCT/EP2017/060475
§ 371 (c)(1),
(2) Date: Oct. 25, 2019

(87) PCT Pub. No.: WO2018/202285
PCT Pub. Date: Nov. 8, 2018

(65) Prior Publication Data
US 2020/0179719 A1    Jun. 11, 2020

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01); *A61N 2005/1087* (2013.01)

(58) Field of Classification Search
CPC .......... A61N 5/1031; A61N 2005/1087; A61N 5/1065; G06F 19/34
See application file for complete search history.

(56) References Cited

U.S. PATENT DOCUMENTS

| | | | |
|---|---|---|---|
| 8,644,571 B1* | 2/2014 | Schulte ................ | A61N 5/1077 382/128 |
| 10,092,774 B1* | 10/2018 | Vanderstraten ...... | A61N 5/1031 |
| 2010/0327188 A1* | 12/2010 | Bert ...................... | A61N 5/1043 250/492.3 |
| 2011/0065974 A1* | 3/2011 | Rietzel .................. | A61N 5/103 600/1 |

(Continued)

FOREIGN PATENT DOCUMENTS

| JP | 2003-070921 A | 3/2003 |
|---|---|---|
| WO | WO-2005/057463 A1 | 6/2005 |

*Primary Examiner* — David P Porta
*Assistant Examiner* — Fani Boosalis
(74) *Attorney, Agent, or Firm* — Faegre Drinker Biddle & Reath LLP

(57) ABSTRACT

A method for ion based radiation therapy treatment planning for avoiding dose delivery to a distal risk organ, said risk organ being located after the target seen from a first beam angle, the method comprising defining an optimization function comprising at least one objective function related to at least one desired property of the treatment plan, wherein the objective function is related to limiting a parameter $\tau$ defining the fraction of the total number $\tau_{OAR}$ of ions that reach the risk organ relative to the total number $\tau_a$ of ions. In addition, one can assume a different density when calculating $\tau$ which will result in a plan that is more robust with respect to density perturbations.

18 Claims, 3 Drawing Sheets

(56) References Cited

U.S. PATENT DOCUMENTS

| | | | |
|---|---|---|---|
| 2012/0187314 A1* | 7/2012 | Bert | A61N 5/1044 |
| | | | 250/492.3 |
| 2013/0077752 A1 | 3/2013 | Zankowski | |
| 2013/0150647 A1* | 6/2013 | Chen | A61N 5/103 |
| | | | 600/1 |
| 2015/0196781 A1 | 7/2015 | Bohsung et al. | |

* cited by examiner

SYSTEM AND METHOD FOR ION BASED RADIOTHERAPY TREATMENT PLANNING

This application is the National Stage of International Application No. PCT/EP2017/060475, filed May 3, 2017, the entire contents of which is incorporated by reference herein.

TECHNICAL FIELD

The present invention relates to a system and a method for ion based radiotherapy treatment planning.

BACKGROUND

In any radiotherapy treatment planning, a main goal is to ensure a prescribed dose (e.g. a uniform dose) to a target volume, such as a tumour, while minimizing the dose to other parts of the patient, and in particular to organs at risk (OAR). Normally, a treatment plan involves delivering radiation from different beam angles. In this document, the terms risk organ, organ at risk and OAR are treated as synonyms.

In proton treatment, dose is delivered to a patient by means of protons that deposit their energy as they travel through the patient's tissues. The distance each proton will travel depends on its energy. Most of the energy is deposited near the end of each proton's trajectory, resulting in a peak in deposited energy known as the Bragg peak, where the highest dose will be delivered. Therefore, dose planning generally attempts to distribute the direction and kinetic energy of the incident protons so that there will be Bragg peaks in all parts of the target. The Bragg peak occurs just before the proton's track end, where it comes to rest. Due to the stochastic nature of energy loss processes, protons having the same incident direction and kinetic energy will suffer not exactly the same energy losses and deflections before they stop. The Bragg peak is therefore broadened into a small 3D volume around its maximum value. Some protons have their track end upstream of the Bragg peak and some downstream of the Bragg peak.

A problem arises where there is a distal OAR, that is, a risk organ located after the target in the direction of the proton's trajectory. There is a risk that some protons travelling in the direction towards the distal OAR, and whose Bragg peaks are located close to the OAR, will reach into the OAR and deposit part of their energy in the OAR. In addition, setup errors and density variations may affect the treatment so that Bragg peaks are displaced to the OAR instead of the target. In regular planning of pencil beam scanning treatment plans, typically the highest weighted energy layers are the most distal ones per beam. In situations where there are distal risk organs close to the target, there is therefore an enhanced conflict between the desire to cover the whole target and the need to protect the risk organ.

Also, the RBE factor increases at the track ends, which means that the energy deposited towards the track ends have a greater biological effect than the same amount of energy deposited at shallower depths. This leads to an increase in the effective range of the proton dose field. The magnitude of the RBE factor is uncertain and often unknown and therefore difficult to include in computations.

Attempts have been made to handle these problems. For example, robust optimization methods may be used. Robustness may also be increased by defining a margin around the clinical target volume CTV. The extended volume is referred to as the PTV and is usually the volume to which dose is prescribed during planning. Another approach is to select beam angles in such a way as to avoid distal risk organs.

SUMMARY

It is an object of the present invention to provide an ion based radiation therapy treatment planning method and system that will avoid delivering dose to risk organs while maintaining a desired dose to a target organ.

The invention proposes a method of optimizing a radiation therapy treatment plan involving causing ions to deliver energy to a portion of the patient from at least a first and a second beam angle, comprising the step of applying an optimization function to a set of patient data. The optimization function comprises a penalty function, such as an objective function or a constraint, related to limiting a parameter $\tau$ defining the fraction of the total number $\tau_{OAR}$ of ions in one or more beams that reach the risk organ relative to a total number $\tau_a$ of ions in said one or more beams.

It should be understood that the parameter $\tau$ can be computed in many ways where the spots included in the definition of the parameter $\tau$ can be selected such as to aid the optimizer to achieve one or several specific goals. For instance, the parameter $\tau$ can be computed per beam or for combinations of beams, using the values $\tau_{OAR}$ and $\tau_a$ per beam. The parameter $\tau$ can also be restricted to include only spots that have an OAR in the spot's direction and be restricted to include a subset of the energy layers for the included beams. For example, only the energy layers that will result in track ends nearest the OAR, typically the highest energy layers, may be considered.

This method introduces the parameter $\tau$ as the fraction of the total number of particles delivered that end up in a particular organ at risk. Adding a penalty function to the objective function limiting this parameter will cause the weights of spots that reach into the OAR with its track ends to be reduced. This means that fewer particles travelling in the direction towards the distal risk organ will have their track ends in a volume near the risk organ or inside the risk organ. To compensate for this, the number of particles delivered by other spots from the same or another beam and depositing energy in that volume will be increased to achieve the prescribed dose. This is possible to achieve if these particles pass the edge of the risk organ without stopping there. Even if some of these ions will deposit energy in the risk organ, for example due to setup errors, their track ends, where the RBE is increased will not be in the risk organ.

Hence, the method ensures that the delivered dose to the volume is as desired while the dose to the organ at risk is guaranteed to be at a low level, by automatically redistributing the dose contribution between the different beams in such a way that the number of track ends in the OAR is minimized.

The penalty function may for example specify that $\tau$ should be kept below a certain threshold value, for example 0.05. Alternatively, the penalty function may specify that $\tau$ should be kept as small as possible. The penalty function may be any suitable penalty function used in treatment plan optimization and may involve a penalty which is linear or a non-linear such as a quadratic penalty. The parameter $\tau$ can also be used as a constraint.

The method may further comprise the step of calculating $\tau$. The parameter $\tau$ may be calculated as the ratio of track ends in the risk organ to the total number of track ends in the patient or in a part of the patient. Alternatively, $\tau$ may be calculated per beam or a combination of beams and relative to the number of track ends from a beam or from all beams or for combinations of beams. Alternatively, the parameter $\tau$ may be calculated only for spots that have an OAR in the spot's direction. In one embodiment, the total number $\tau_{OAR1}$ of ions from the first beam angle that reach a risk organ, and the total number $\tau_{a1}$ of ions from the first beam angle, are used to calculate $\tau=\tau_{OAR1}/\tau_{a1}$.

Further advantages may be achieved if the calculation to determine the location of the track ends is performed based on a density that is different from the actual density in the tissue traversed by the ions. In one preferred embodiment, the calculation to determine the location of the track ends is performed based on a somewhat lower density than the actual density in the tissue traversed by the ions. As a result of this, the optimization will be based on an overestimated value of $\tau$. This will lead to an increased suppression of the weights of those spots that are at risk of reaching the OAR. This will limit the ions depositing energy in the risk organ at their track ends. As explained above, the energy deposited near the track ends has a higher relative biological effect, so it is especially desirable to avoid such ions in the risk organ. The dose from the other beam may be able to compensate for this either partly or completely, and will not be affected by the changed tissue density.

Alternatively, the location of the track ends may be based on a somewhat higher density than the actual density traversed by the ions. This may be advantageous in cases where track ends are undesirable upstream of a target volume. For instance, it can in some situations be necessary to use a beam with an OAR upstream of the target. Similar to the more common case with the OAR downstream of the target it is desirable to keep the number of track ends to a minimum in the OAR. In this case, the energy layers closest to the OAR will be the lowest energy layers.

The invention also relates to a computer program product comprising computer-readable code means which, when run in a computer, will cause the computer to perform the method according to any one of the preceding claims. The computer program product may be stored on a carrier, such as a non-transitory storage medium. The invention also relates to a computer system comprising a processor and a program memory, the program memory holding such a computer program product in such a way that it can be executed by the processor. The invention further relates to a treatment planning system comprising such a computer system.

BRIEF DESCRIPTION OF THE DRAWINGS

The invention will be described in more detail in the following, by way of example and with reference to the appended drawings, in which.

DETAILED DESCRIPTION

Figure 1A:
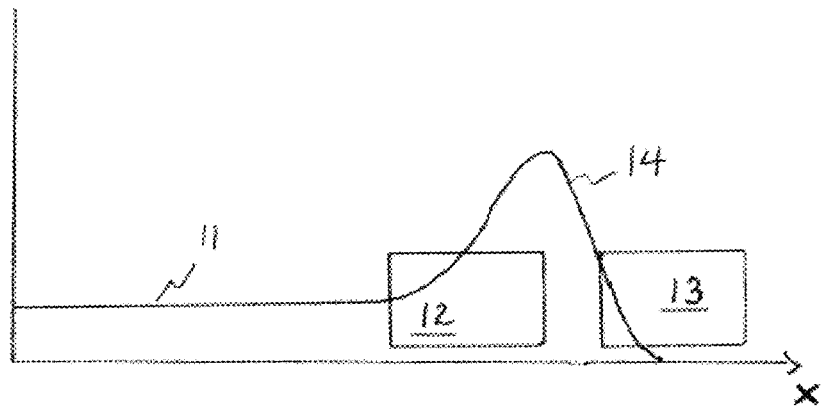
FIGS. 1a-1c illustrate the beam trajectory, the Bragg peak, the RBE factor and the distribution of track ends.

FIG. 1a illustrates the deposited energy along the trajectory of an ion, such as a proton, traversing a portion of a patient, as a function of the distance x. The positions of a target 12 and an organ at risk 13 are indicated by a first and a second box, respectively. As can be seen, the Bragg peak, in which the main portion of the energy is deposited, is positioned close to the distal end of the target 12 seen from the source of the radiation. As can also be seen, the ion will continue to deposit energy after it has traversed the target 12 and will deposit the last of its energy in the risk organ 13.

Figure 1B:
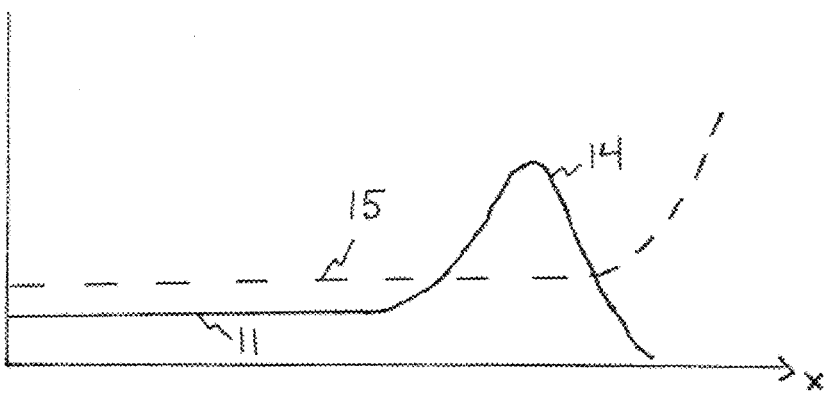

It is known that the relative biological effectiveness RBE of the energy deposited after the Bragg peak is greater than the RBE of the energy deposited earlier. This effect is illustrated in FIG. 1b, which shows the same curve for deposited energy as in FIG. 1a, as a solid line and the RBE as a dashed line. Along most of the particle trajectory the RBE is approximately 1.1, increasing towards the end to values that are difficult to predict but that may be as high as 1.6. This means that a relatively low dose deposited near the track end will have a larger biological effect than a corresponding dose deposited earlier.

Figure 1C:
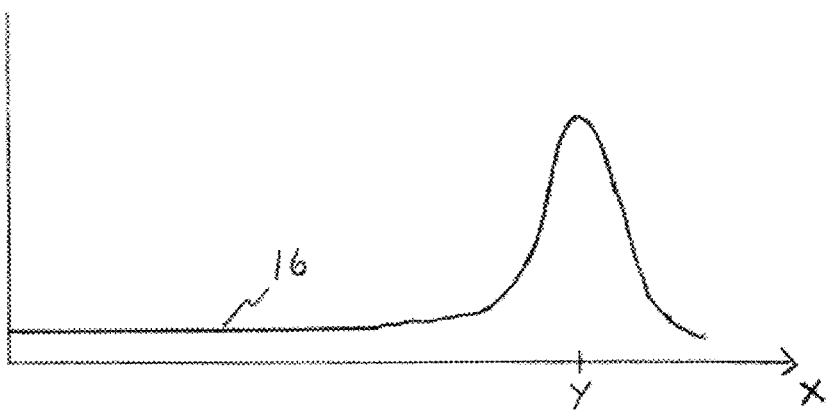

FIG. 1c shows the distribution of track ends as a function of the distance travelled, that is, the position where the ions stop in the patient. As can be seen, the track end position cannot be predicted with 100% accuracy. Instead the track end positions will have a Gaussian like distribution.

Figure 2:
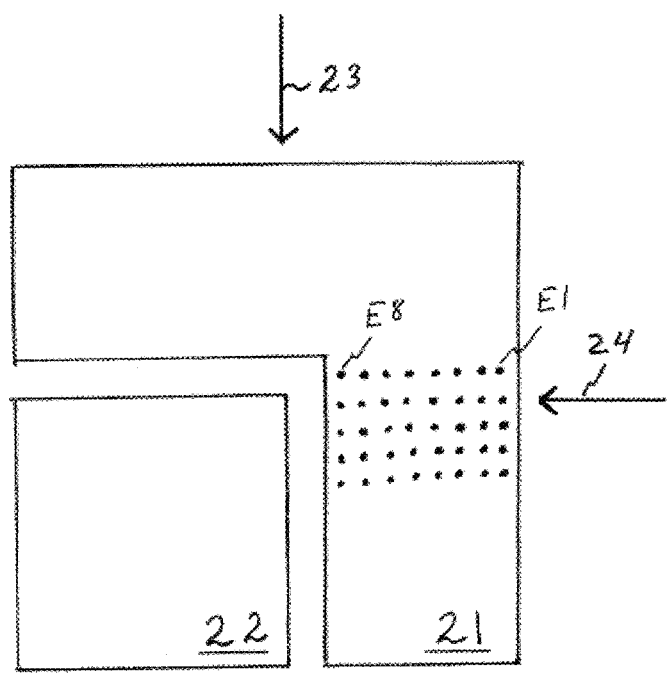
FIG. 2 illustrates a schematic patient having an organ at risk adjacent to a target.

FIG. 2 illustrates schematically a situation in which a target 21, such as a tumour, encloses on two sides an organ at risk 22. Such a situation may occur, for example, in the case of a brain tumour growing near the brain stem. Typically in such a case, radiation will be delivered from at least two beam angles, to maximize the dose to the target while minimizing the dose to the risk organ 22. In this example, typical beam angles would be from above in the Figure, as indicated by the vertical arrow 23 and from the right in the Figure, as indicated by the horizontal arrow 24.

In pencil beam scanning, the treatment plan is specified by a number of energy layers where each layer contains a number of pencil beam spots of a given weight. Each spot has its Bragg peak somewhere in the target at a depth which is determined by the energy layer. The Bragg peaks are indicated by dots in FIG. 2, and are distributed across the volume to be treated. The Bragg peaks will be defined in different energy layers, the layer having the lowest energy corresponding to the Bragg peaks closest to the radiation source denoted E1 in the Figure, and the layer having the highest energy corresponding to the Bragg peaks farthest from the radiation source, denoted E8 in the Figure. The particles in the energy layer E8 and with positions in front of the risk organ are the ones that have the highest risk of also depositing energy in the risk organ. As discussed above, this may happen if the patient moves slightly relative to the radiation source, or if the density of the tissue traversed by the particles is different from the density values used in planning. There is also an effect known as straggling, which means that the energy deposited by two particles that traverse the same part of the patient and have the same energy will vary along a trajectory. They will therefore stop at different positions.

Figure 3:
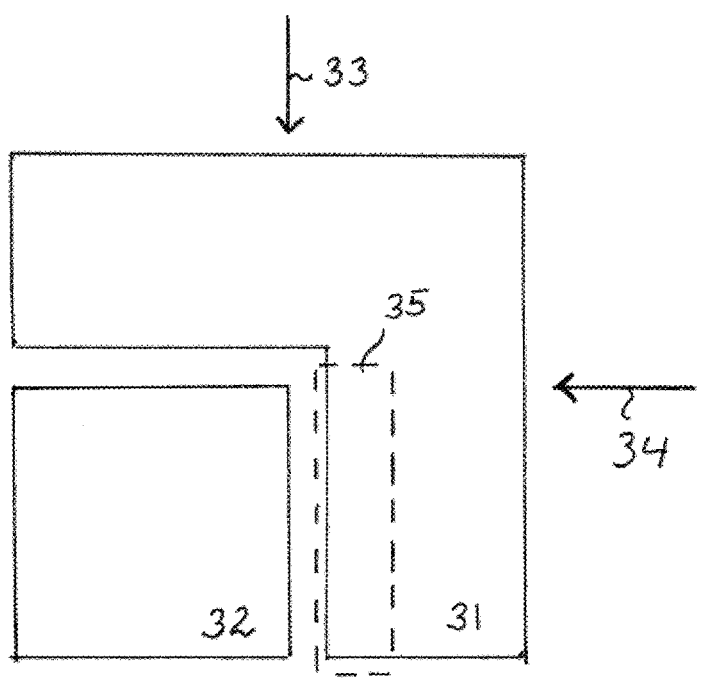
FIG. 3 illustrate the track ends resulting from treatment planning.

FIG. 3 illustrates the same schematic situation as in FIG. 2, with a target 31, a risk organ 32 and a first and a second beam angle 33, 34, respectively. For the following discussion, the contribution from the horizontal beam angle 34 will be considered. An area 35 is indicated at the distal side of the portion of the target 11 adjacent the risk organ 32. This area suitably corresponds roughly to the area that will be reached by the spots that belong to a particular energy layer. This layer has an energy which is determined so that the spots reach the distal part of the target 31 without reaching in to the risk organ. The beam 34 has additional energy layers to reach the deeper laying parts of the upper part of the target volume. For these higher energy layers, there are no spots with Bragg peaks in the risk organ 32.

The parameter τ as used in the model is defined as:

τ: the fraction $\tau_{OAR}/\tau_a$, where $\tau_a$ is the total number of ions (=total number of track ends) in the two beams, and $\tau_{OAR}$: the number of ions with track ends inside the OAR volume. A typical value for τ in traditional treatment planning is 0.2, which means that approximately 20% of the ions reach the risk organ.

In a particular embodiment, the parameter τ as used in the model is defined as

τ: the fraction $\tau_{OAR1}/\tau_{a1}$, where $\tau_{OAR1}$ is the total number of ions from the first beam angle that reach a risk organ, $\tau_{a1}$ is the total number of ions from the first beam angle.

It may be preferable to calculate T based on a subset of the energy layers for the included beam or beams. For example in the situation depicted in FIG. 2, only the energy layer E8 closest to the risk organ, or the n layers closest to the risk organ could be considered, n being an integer 1-7. In an opposite situation, where the risk organ was located upstream of the target, the energy layer E1, or a number of consecutive layers starting with E1 could be considered.

The track end penalty function may be of various kinds similar to penalty function used for radiotherapy treatment plan optimization. Thus, the optimization problem may be formulated as "keep τ as small as possible" or "keep τ below a threshold value". The threshold value can be a fix value or may be set in dependence of what is deemed to be realistic, for example 5% or 7%. The penalty may be linear or non-linear, for example quadratic or exponential. The track end penalty function is typically part of a total objective function where the goal of the optimization is to minimize the total objective function value. Alternatively, the track end penalty function may be applied as a constraint that must be fulfilled.

The effect of limiting the fraction of the ions that is allowed to reach the risk organ 32 by means of an objective function is that the weight assigned to the spots that reach the risk organ will be decreased. Looking at the ions coming in from the right-hand side of FIGS. 2 and 3, there will be fewer ions in the energy layer E8, so that this beam angle will contribute less to the dose in the area 35 of the target 31 adjacent to the risk organ 32. To compensate for the resulting reduction in dose in this volume from this beam, the number of ions in this area from the vertical beam angle 33 coming from above in FIG. 3 will be increased. This will be handled automatically by the optimization function. There is a risk that some ions traversing the area 35 from the vertical beam angle 33 will deposit energy in the risk organ 32, for example, because of setup errors. This energy deposition will not take place at the track ends for the respective particle, and therefore will not have the elevated RBE value. Therefore, the same energy deposition will lead to less damage. This is advantageous as this dose may be calculated more exactly as there is less uncertainty in the RBE factor because there are no track ends.

A further advantage is achieved if the planning is performed assuming somewhat lower density values when calculating r than the actual density values for the traversed tissue. This will cause the optimization to reduce further the ions that are at risk of reaching into the OAR volume through volume 35. Hence, the plan is more robust with respect to density perturbations.

Figure 4:
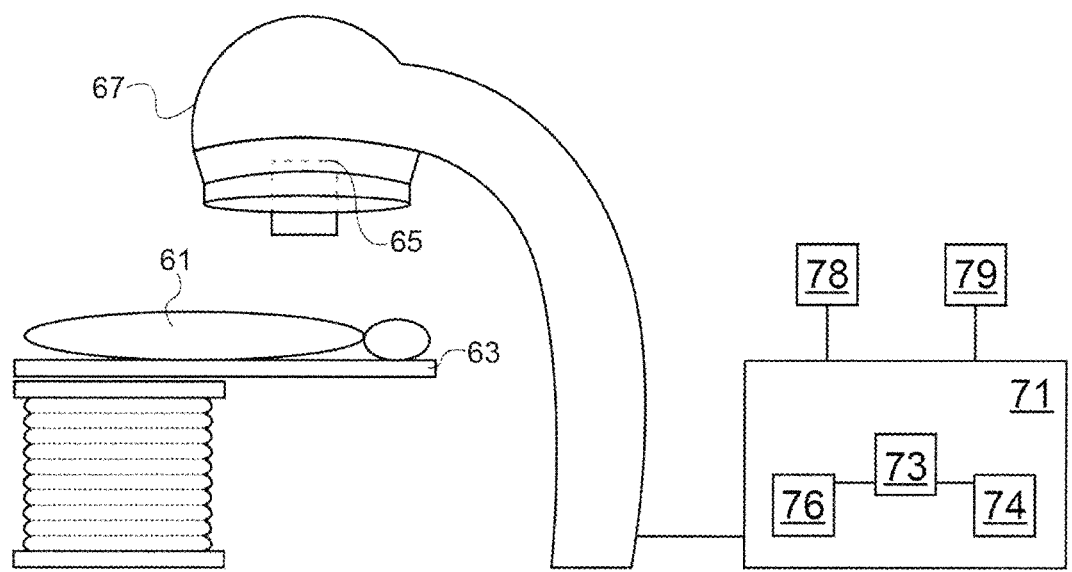
FIG. 4 is an overview of a system for radiotherapy treatment and/or planning.

FIG. 4 is an overview of a system for radiotherapy treatment and/or planning. As will be understood, such systems may be designed in any suitable way and the design shown in FIG. 4 is only an example. A patient 61 is positioned on a treatment couch 63. The system comprises a radiation source 65 mounted in a gantry 67 for emitting radiation towards the patient positioned on the couch 63. Typically, the couch 63 and the gantry 67 are movable in several dimensions relative to each other, to enable radiation to be delivered to the patient as flexibly and correctly as possible. These parts are well known to the skilled person. The system also comprises a computer 71 which may be used for radiotherapy treatment planning and/or for controlling radiotherapy treatment. As will be understood, the computer 71 may be a separate unit not connected to the treatment unit.

The computer 71 comprises a processor 73, a data memory 74, and a program memory 76. Preferably, one or more user input means 78, 79 are also present, in the form of a keyboard, a mouse, a joystick, voice recognition means or any other available user input means. The user input means may also be arranged to receive data from an external memory unit.

The data memory 74 comprises clinical data and/or other information used to obtain a treatment plan, including a set of clinical goals to be used for planning. The data memory 74 also comprises one or more dose maps for one or more patients to be used in treatment planning according to embodiments of the invention. The program memory 76 holds a computer program, known per se, including the optimization function and arranged for treatment plan optimization.

Optimization based on minimizing an objective function is well known in the art. In this case, the objective function includes an objective function based on limiting τ as discussed above.

As will be understood, the data memory 74 and the program memory 76 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

The invention claimed is:

1. A method of optimizing a radiation therapy treatment plan involving causing ions to deliver energy to a portion of a patient from at least a first and a second beam angle, the method comprising:

applying an optimization function to a set of patient data, wherein the optimization function comprises a penalty function, including an objective function or a constraint, related to limiting a parameter τ defining a fraction of a total number $\tau_{OAR}$ of ions in at least two beams, including a first beam delivered from the first beam angle and a second beam delivered from the second beam angle, that reach a risk organ relative to a total number $\tau_a$ of ions in said at least two beams delivered from at least the first and the second beam angles, wherein application of the optimization function provides an optimized radiation therapy treatment plan configured to deliver, by a radiation source, radiation to the portion of the patient while reducing an amount of radiation to the risk organ.

2. The method according to claim 1, wherein the penalty function specifies that $\tau$ should be kept below a threshold value of 0.05.

3. The method according to claim 1, wherein the penalty function specifies that $\tau$ should be kept as small as possible.

4. The method according to claim 1, wherein a total number $\tau_{OAR1}$ of ions from the first beam angle that reach a risk organ, and a total number $\tau_{a1}$ of ions from the first beam angle, are used to calculate $\tau = \tau_{OAR1}/\tau_{a1}$.

5. The method according to claim 1, further comprising calculating $\tau$ as the ratio of a number of track ends in the risk organ to a total number of track ends in the patient or in the portion of the patient.

6. The method according to claim 1, further comprising calculating $\tau$ per beam or a combination of beams and relative to a number of track ends from the beam or the combination of beams.

7. The method according to claim 1, wherein $\tau$ is calculated based on a subset of the energy layers for the included beam or beams.

8. The method according to claim 1, wherein the penalty function involves a linear penalty or a non-linear penalty, including a quadratic penalty.

9. The method according to claim 1, wherein the radiotherapy treatment planning takes into account a planning density value lower than the actual density of the portion of the patient when calculating $\tau$.

10. The method according to claim 1, wherein the radiotherapy treatment planning takes into account a planning density value higher than the actual density of the portion of the patient when calculating $\tau$.

11. A non-transitory computer-readable storage medium storing therein computer-readable code which, when run in a computer, causes the computer to perform the method according to claim 1.

12. A computer system comprising a processor and a non-transitory computer-readable storage medium storing therein instructions which, when run on the processor, cause the processor to perform the method according to claim 1.

13. A treatment planning system comprising a computer system according to claim 12.

14. A method of optimizing a radiation therapy treatment plan involving causing ions to deliver energy to a portion of a patient from at least a first and a second beam angle, the method comprising:
applying an optimization function to a set of patient data, wherein the optimization function comprises a penalty function, including an objective function or a constraint, related to limiting a parameter $\tau$ defining a fraction of a total number $\tau_{OAR}$ of ions in one or more beams that reach a risk organ relative to a total number $\tau_a$ of ions in said one or more beams, wherein a total number $\tau_{OAR1}$ of ions from the first beam angle that reach a risk organ, and a total number $\tau_{a1}$ of ions from the first beam angle, are used to calculate $\tau = \tau_{OAR1}/\tau_{a1}$, wherein application of the optimization function provides an optimized radiation therapy treatment plan configured to deliver, by a radiation source, radiation to the portion of the patient while reducing an amount of radiation to the risk organ.

15. A method of optimizing a radiation therapy treatment plan involving causing ions to deliver energy to a portion of a patient from at least a first and a second beam angle, the method comprising:
applying an optimization function to a set of patient data, wherein the optimization function comprises a penalty function, including an objective function or a constraint, related to limiting a parameter $\tau$ defining a fraction of the total number $T_{OAR}$ of ions in one or more beams that reach a risk organ relative to a total number $\tau_a$ of ions in said one or more beams; and
calculating $\tau$ as the ratio of a number of track ends in the risk organ to a total number of track ends in the patient or in the portion of the patient, wherein application of the optimization function provides an optimized radiation therapy treatment plan configured to deliver, by a radiation source, radiation to the portion of the patient while reducing an amount of radiation to the risk organ.

16. A method of optimizing a radiation therapy treatment plan involving causing ions to deliver energy to a portion of a patient from at least a first and a second beam angle, the method comprising:
applying an optimization function to a set of patient data, wherein the optimization function comprises a penalty function, including an objective function or a constraint, related to limiting a parameter $\tau$ defining a fraction of a total number $T_{OAR}$ of ions in one or more beams that reach a risk organ relative to a total number $\tau_a$ of ions in said one or more beams; and
calculating $\tau$ per beam or a combination of beams and relative to a number of track ends from the beam or the combination of beams, wherein application of the optimization function provides an optimized radiation therapy treatment plan configured to deliver, by a radiation source, radiation to the portion of the patient while reducing an amount of radiation to the risk organ.

17. A method of optimizing a radiation therapy treatment plan involving causing ions to deliver energy to a portion of a patient from at least a first and a second beam angle, the method comprising:
applying an optimization function to a set of patient data, wherein the optimization function comprises a penalty function, including an objective function or a constraint, related to limiting a parameter $\tau$ defining a fraction of a total number $\tau_{OAR}$ of ions in one or more beams that reach a risk organ relative to a total number $\tau_a$ of ions in said one or more, wherein application of the optimization function provides an optimized radiation therapy treatment plan configured to deliver, by a radiation source, radiation to the portion of the patient while reducing an amount of radiation to the risk organ, wherein the radiotherapy treatment planning takes into account a planning density value lower than the actual density of the portion of the patient when calculating $\tau$.

18. A method of optimizing a radiation therapy treatment plan involving causing ions to deliver energy to a portion of a patient from at least a first and a second beam angle, the method comprising:
applying an optimization function to a set of patient data, wherein the optimization function comprises a penalty function including an objective function or a constraint, related to limiting a parameter $\tau$ defining a fraction of a total number $\tau_{OAR}$ of ions in one or more beams that reach a risk organ relative to a total number $\tau_a$ of ions in said one or more beams, wherein application of the optimization function provides an optimized radiation therapy treatment plan configured to deliver, by a radiation source, radiation to the portion of the patient while reducing an amount of radiation to the risk organ, wherein the radiotherapy treatment planning takes into account a planning density value higher than the actual density of the portion of the patient when calculating $\tau$.

* * * * *